(12) United States Patent
Hitzenberger

(10) Patent No.: US 7,145,661 B2
(45) Date of Patent: Dec. 5, 2006

(54) EFFICIENT OPTICAL COHERENCE TOMOGRAPHY (OCT) SYSTEM AND METHOD FOR RAPID IMAGING IN THREE DIMENSIONS

(75) Inventor: Christoph K. Hitzenberger, Viienna (AT)

(73) Assignee: Carl Zeiss Meditec, Inc., Dublin, CA (US)

( * ) Notice: Subject to any disclaimer, the term of this patent is extended or adjusted under 35 U.S.C. 154(b) by 291 days.

(21) Appl. No.: 10/750,341

(22) Filed: Dec. 31, 2003

(65) Prior Publication Data

US 2005/0140984 A1    Jun. 30, 2005

(51) Int. Cl.
    *G01B 11/02*   (2006.01)
(52) U.S. Cl. ..................................... 356/497
(58) Field of Classification Search .............. 356/479, 356/491, 492, 495, 497, 511, 512, 513, 514
    See application file for complete search history.

(56) References Cited

U.S. PATENT DOCUMENTS

| | | | | |
|---|---|---|---|---|
| 4,798,468 | A | * | 1/1989 | Ohuchi ..................... 356/495 |
| 4,869,593 | A | * | 9/1989 | Biegen ..................... 356/495 |
| 5,202,745 | A | | 4/1993 | Sorin et al. ................ 356/73.1 |
| 5,321,501 | A | | 6/1994 | Swanson et al. ............ 356/345 |
| 5,459,570 | A | | 10/1995 | Swanson et al. ............ 356/345 |
| 5,847,827 | A | * | 12/1998 | Fercher ..................... 356/497 |
| 5,975,697 | A | | 11/1999 | Podoleanu et al. ......... 351/206 |
| 6,134,003 | A | | 10/2000 | Tearney et al. ............. 356/345 |
| 6,137,585 | A | | 10/2000 | Kitzenberger et al. ...... 356/484 |
| 6,385,358 | B1 | | 5/2002 | Everett et al. .............. 385/12 |
| 6,615,072 | B1 | | 9/2003 | Izatt et al. .................. 600/478 |
| 6,657,727 | B1 | | 12/2003 | Izatt et al. .................. 356/450 |

OTHER PUBLICATIONS

Barnoski, J. K., S. M. Jensen. "Fiber waveguides: A novel technique for investigation attenuation characteristics." *Appl. Opt.*, 15, pp. 2112-2115 (1976).

Fercher, A. F., C. K. Hitzenberger. "Optical Coherence Tomography." Chapt. 4 in *Progress in Optics*, 44, Elsevier Science B.V. (2002).

Hitzenberger, C. D., P. Trost, P. W. Lo, and O. Zhou. "Three-dimensional imaging of the human retina by high-speed optical coherence tomography." *Opt. Express*, 11, pp. 2753-2761 (Oct. 2003).

Hoeling, B., A. Fernandez, R. Haskell, E. Huang, W. Myers, O. Peterson, S. Ungersma, R. Wang, M. Williams and S. Fraser. "An optical coherence microscope for 3-dimensional imaging in developmental biology." *Opt. Express*, 6, pp. 136-145 (2000).

(Continued)

*Primary Examiner*—Gregory J. Toatley, Jr.
*Assistant Examiner*—Michael A. Lyons
(74) *Attorney, Agent, or Firm*—Stallman & Pollock LLP

(57) ABSTRACT

An optical coherence tomography (OCT) system including a polarizing splitter disposed to direct light in an interferometer such that the OCT detector operates in a noise-optimized regime. When scanning an eye, the system detector simultaneously produces a low-frequency component representing a scanning laser ophthalmoscope-like (SLO-like) image pixel and a high frequency component representing a two-dimensional (2D) OCT en face image pixel of each point. The SLO-like image is unchanging with depth, so that the pixels in each SLO-like image may be quickly realigned with the previous SLO-like image by consulting prominent image features (e.g., vessels) should lateral eye motion shift an OCT en face image during recording. Because of the pixel-to-pixel correspondence between the simultaneous OCT and SLO-like images, the OCT image pixels may be remapped on the fly according to the corresponding SLO-like image pixel remapping to create an undistorted 3D image data set for the scanned region.

30 Claims, 9 Drawing Sheets

OTHER PUBLICATIONS

Huang, D., E. A. Swanson, C. P. Lin, J. S. Schuman, W. G. Stinson, W. Chang, M. R. Hea, T. Flotte, K. Gregory, C. A. Puliafito, et al. "Optical Coherence Tomography." *Science*, 254, pp. 1178-1181 (Nov. 1991).

Kompfner, R., H. Park. "High-resolution heterodyne coincidence detection of optical pulse streams." *Int. J. Electron.*, 41, pp. 317-323 (1976).

Park, H., M. Chodorow, R. Kompfner. "High Resolution Optical Ranging System." *Appl. Opt.*, 20, pp. 2389-2394 (Jul. 1981).

Podoleanu, A. Gh., D. A. Jackson. "Noise Analysis of a Combined Optical Coherence Tomography and a Confocal Scanning Ophthalmoscope." *Appl. Optics*, 38 pp. 2116-2117 (Apr. 1999).

Podoleanu, A. Gh., J. A. Rogers, D. A. Jackson, S. Dunne. "Three dimensional OCT images from retina and skin." *Opt. Express*, 7, pp. 292-298 (2000).

Rollins, A. M., J. A. Izatt. "Optimal interferomater designs for optical coherence tomography." *Opt. Lett.*, 24, pp. 1484-1488 (Nov. 1999).

Rogers, J. A., A. Gh. Podoleanu, G. M. Dobre, D. A. Jackson, F W. Fiske. "Topography and volume measurements of the optic nerve using *en-face* optical coherence tomography." *Optics Express*, 9, pp. 533-545, (Nov. 5, 2001).

Youngquist, R. C., S. Carr, D. E. N. Davies. "Optical coherence-domain reflectometry: a new optical evaluation technique." *Opt. Lett.*, 12, pp. 158-160 (Mar. 1987).

* cited by examiner

EFFICIENT OPTICAL COHERENCE TOMOGRAPHY (OCT) SYSTEM AND METHOD FOR RAPID IMAGING IN THREE DIMENSIONS

BACKGROUND OF THE INVENTION

1. Field of the Invention

This invention relates generally to optical coherence tomography (OCT) systems for three-dimensional (3D) imaging and more particularly to a power-efficient OCT system and method for rapid 3D ocular imaging without motion artifacts.

2. Description of the Related Art

The optical coherence tomography (OCT) art has evolved over time from the optical time-domain reflectometry (OTDR) art described by Barnoski et al. in 1976 [J. K. Barnoski, S. M. Jensen, "Fiber waveguides: A novel technique for investigation attenuation characteristics," *Appl. Opt.*, 15, 2112-5 (1976)]. OTDR was first employed to measure the elapsed time (t) and intensity of light reflected along a SINGLE path in optical fiber to determine the distance (d=ct) to problems along the fiber such as attenuation and breaks, making it a useful tool in optical network trouble-shooting. The original idea of OTDR consists in launching a rather short and high power optical impulse into the tested fiber and a consequent incoherent detection of optical power backscattered along the z-axis of the fiber as a response to the test impulse. The detected signal provides the detailed picture of the local loss distribution along the fiber caused by any of the attenuation mechanisms or some other nonhomogeneities on the fiber. In the same year, Kompfner et al. [. Kompfner and H. Park, *Int. J. Electron.*, 41, 317 (1976)] proposed a system for the coherent detection of a series of such backscattered pulses to see through otherwise opaque material.

Several years later, in 1981, Park et al. [H. Park, M. Chodorow, and R. Kompfner, "High Resolution Optical Ranging System," *Appl. Opt.*, 20, 2389-94 (July 1981)] reported experimental results for the Kompfner et al proposal, which adapts the incoherent OTDR technique by splitting the short and powerful optical impulse signal into TWO physical channels and combining the optical power backscattered from a reference mirror with that backscattered from a test sample. Using coherent detection, Park et al. were able to measure test sample reflections from the particular test sample z-axis locus corresponding to the reference mirror position on the z-axis. Axial motion of the reference mirror serves to move the test sample reflection detection locus along the z-axis. This OTDR technique was denominated coherent OTDR (CO-OTDR) by some practitioners. Park et al. were able to achieve 1.7 mm z-axis resolution and proposed the addition of two-dimensional (2D) scanning means to permit three-dimensional imaging in an otherwise opaque test sample. This proposal may be properly denominated "tomography," which denotes "an imaging technique using sections or planes to visualize the interior" of a test sample.

Thereafter, in 1987, Youngquist et al. [R. C. Youngquist, S. Carr, and D. E. N. Davies, "Optical coherence-domain reflectometry: a new optical evaluation technique," *Opt. Lett.*, 12, 158–160 (March 1987)] first proposed a modification of the CO-OTDR technique using a continuous wave optical source signal having a short coherence length. They denominated their incoherent source method "optical coherence-domain reflectometry (OCDR)." The OCT denomination later appeared in the art [e.g., Huang et al., "Optical Coherence Tomography," *Science*, 254, 1178–81 (November 1991)]. With OCDR, the output signal from an incoherent optical source is said to have a "short coherence length" when its autocorrelation function has a single peak that is relatively narrow in time. The OCDR method splits the incoherent signal into two channels and combines the reflections from a reference mirror and a test sample at a detector where the signals interfere to form fringes whose intensity represent the reflectance from a volumetric region of the test sample at a position on the z-axis defined by the reference mirror position, the extent of which is defined in the xy plane by a focus area and in depth on the z-axis by the signal coherence length. A transverse scanner can be added to map this reflectance over a transverse "slice" of the test sample in the xy plane. Mapping a series of these xy slices by moving the reference mirror along the z-axis results in a three-dimensional image (tomography) of an internal test sample volume (3D-OCT).

Since 1987, numerous practitioners have proposed improvements to the OCT art, many of which are discussed in a review by Fercher et al. [A. F. Fercher, C. K. Hitzenberger, "Optical coherence tomography," Chapter 4 in *Progress in Optics* 44, Elsevier Science B.V. (2002)]. Although the OCT art offers many advantages for biological tissue mapping, especially in the eye, many practical problems have been identified over the years, such as those relating to the design of practical interferometric scanning and detection systems, generation of partially coherent fields, improved detection (scan) speeds, and the elimination of movement artifacts arising from involuntary eye movement during scanning.

FIG. 1 illustrates a typical OCT scanner 12 from the prior art. The interferometer 13 splits a signal S from a broadband source 14 into a reference signal $S_R$ and a sample signal $S_S$. The reference signal $S_R$ is directed to a reference reflector 16 disposed to move in either direction along the z-axis and the sample signal $S_S$ focuses through the scanning optics 18 and the objective lens 20 to some point 22 within the test sample 24 under test (e.g., tissue). After scattering back from point 22 in test sample 24, the modified sample field $E_S$ mixes with the reflected reference signal field $E_R$ on the surface of a photodetector 26. Assuming that photodetector 26 captures half of the light from the reference and sample arms of interferometer 13 (the other half returns to the source if a normal 50:50 beam splitter is used), the signal intensity impinging on photodetector 26 is $$I_D = \langle |S_D|^2 \rangle = 0.5(I_R + I_S) + Re\{\langle E_R^*(t+\tau) E_S(t)\rangle\} \equiv I_{DC} + I_{PIX} \quad [\text{Eqn 1}]$$

where $I_R$ and $I_S$ are the mean (DC) intensities of the reflected signals returning from the reference and sample arms of the interferometer. The second term in Eqn. 1 is the cross-correlation signal $I_{PIX}$, which depends on the optical time delay $\tau$ established by the z-axis position of reference reflector 16 and represents the amplitude of the interference fringes that carry information about the structure of point 22 in test sample 24; the envelope of this fringe signal may correspond to a single "pixel" in a 2D image of test sample 24. The presence and nature of these interference fringes depends on the alignment of the temporal and spatial characteristics of the reflected fields $E_S$ and $E_R$. Thus, interferometer 13 functions as a cross-correlator and the amplitude $I_{PIX}$ of interference signal generated after integration on the surface of detector 26 provides a measure of the cross-correlation amplitude. The z-axis thickness of point 22 depends on the coherence length of broadband signal S. Various techniques are known in the art for modulating $\tau$ (e.g. by vibrating reflector 16) to facilitate separation of the cross-correlation signal $I_{PIX}$ from the mean component $I_{DC}$ of intensity $I_D$ at detector 26 (the first term of Eqn. 1). When $I_{DC}$ greatly exceeds $I_{PIX}$, the detector may be operating in the excess intensity noise regime where the effective signal-to-noise ratio (SNR) is degraded. Movement of mirror 16 along the z-axis facilitates measurement of reflectance from test sample 24 at numerous points along the z-axis. Scanning optics 18 may be arranged to facilitate scanning of en face images over a 2D (xy) plane within test sample 24 at various (usually sequential) z-axis locations.

As shown in FIG. 2 from the prior art, any of several scanning patterns may be used to obtain three-dimensional (3D) image data sets with OCT scanner 12. Most practitioners refer to a longitudinal imaging procedure wherein the longitudinal scan lines directed along the z-axis in the image correspond to A-scans and the transverse scan along the x-axis in FIG. 2 (or the y-axis) advances at a slower pace to build the B-scan image 28 illustrated at the top of FIG. 2. This may be reversed so that the transverse scanner produces the fast lines in the image and the longitudinal scanner advances more slowly to build the B-scan image 30 illustrated in the middle of FIG. 2, which simplifies the production of transverse en face images for a fixed reference path, such as the en face image 32 illustrated in FIG. 1 bottom. A first transverse scanner scans the test sample along the lines (x-axis) in image 32 while a second transverse scanner advances more slowly along the second co-ordinate (y-axis) in image 32. A transverse slice (en face image) is thereby collected at each of several different depths on the z-axis, either by advancing the optical path difference in steps after each complete transverse scan or continuously at a speed for which the depth position of the point in the top left corner of the image and the depth position in the bottom right corner of the image do not differ by more than half the depth resolution. This provides one of the fastest methods for recording a 3D image data set for a region within sample 24.

Recording a single typical 3D image of, e.g., the retina of a human eye, requires at least one second of scanning time in the present art. Involuntary eye movements occurring during this recording period may introduce distortions into the 3D image data, and consequently, may distort and degrade any 2D diagnostic images derived from such data. For example, Podoleanu et al [A. Gh. Podoleanu, J. A. Rogers, D. A. Jackson, S. Dunne, "Three dimensional OCT images from retina and skin," Opt. Express, 7, 292–298 (2000)] suggest that en face OCT images are preferred for reasons of speed but also prone to "blurring" arising from test sample motion. In the commonly-assigned U.S. Pat. No. 6,137,585, entirely incorporated herein by reference, Hitzenberger describes a differential OCT system in which artifacts arising from z-axial components of sample motion can be eliminated by using a reference reflector defined by the sample (e.g., the cornea in ocular OCT imaging) that moves along the z-axis with the sample. However, this method is not useful for eliminating artifacts arising from transverse (xy plane) components of sample motion generally.

Transverse motion artifacts are embodied as misalignment of sequential transverse slices (en face images) recorded at different sample depths and thus may be eliminated by detecting and aligning image features of sequential transverse images, provided these features are present in several sequential images. Because of the very narrow depth of each OCT image slice and the curvature of the retina, transverse OCT images of the retina have a fragmented appearance that makes it difficult to find common features in sequential images. This problem is well-appreciated in the art and has been addressed by several practitioners.

For retinal imaging, some have suggested that the motion artifact alignment problem can be resolved by recording, in parallel to each OCT slice, a separate image with the wider depth range needed to reveal test sample features sufficient to guide any realignment of the OCT slices necessary to remove motion artifacts. Such a second image may be obtained, e.g., by employing a separate detector operating in a scanning laser ophthalmoscope (SLO). In principle, the SLO images may reveal the precise timing and degree of any transverse eye motion after scan completion with the help of visible landmark features common in each of these images.

In U.S. Pat. No. 5,975,697, Podoleanu et al. describe an optical mapping apparatus for measuring en face images with adjustable depth to permit correction of the images for curvature of the retina at the back of the lens of the eye. Podoleanu et al. describe the many considerable difficulties with using OCT and SLO en face images in parallel and suggest elaborate procedures intended to eliminate some of these problems, including readjusting the SLO image depth resolution, recording OCT slices at several different resolutions, and employing common receiver optics for both OCT and SLO image channels. Podoleanu et al. suggest that their elaborate procedures, while slow, may permit the useful comparison of OCT retinal image data to existing SLO image databases for medical diagnosis. Disadvantageously, with this method, part of the source light power must be diverted to a separate SLO detector, decreasing the SNR of the OCT image channel. Podoleanu and Jackson [A. Gh. Podoleanu, D. A. Jackson, "Noise Analysis of a Combined Optical Coherence Tomograph and a Confocal Scanning Ophthalmoscope," Appl. Optics, 38, 2116–7, April 1999] suggest that their OCT channel SNR must be traded off to permit the simultaneous acquisition of OCT and SLO en face images. They also note the speed penalty associated with this SNR degradation and with their method of combining OCT and SLO images of the retina. Moreover, this method disadvantageously requires an additional detector, amplifier, and frame grabber to avoid the detector SNR limitations encountered in the excess intensity noise dominated regime. Later, Rogers et al [J. A. Rogers, A. Gh. Podoleanu, G. M. Dobre, D. A. Jackson and F. W. Fiske, "Topography and volume measurements of the optic nerve using en-face optical coherence tomography," Optics Express, 9, 533–45, 05 Nov. 2001] describe an application of the en-face OCT scanning technique to optic nerve topography. While Rogers et al. stated that the confocal channel was not absolutely necessary, it greatly helped to track the relative eye movements in the OCT en face images. For this purpose, Rogers et al. also require a separate detector and beam splitter to record their OCT signal and they observe that further study is needed to determine the optimum number of frames to be superposed to realize the best advantages of their suggested method. Their additional beam splitter diverts part of the available light away from the OCT receiver, which reduces the light power reaching the OCT detector via the sample arm and thereby reduces the sensitivity of the OCT detector channel.

More recently, Hitzenberger et al. [C. K. Hitzenberger, P. Trost, P. W. Lo, and Q. Zhou, "Three-dimensional imaging of the human retina by high-speed optical coherence tomography," Opt. Express, 11, 2753–61 (October 2003)] suggest generation of SLO-like images by projection of the transversal OCT image slices on top of each other, thereby avoiding the necessity of the second or parallel SLO imaging channel suggested in earlier publications. The proposed SLO-like images do not require a second detector so the OCT channel sensitivity is unaffected thereby but these SLO-like images are still somewhat distorted by movement artifacts, and therefore cannot be used to re-align 3D OCT image data.

Useful solutions to the OCT motion artifact problem are limited by several well-known OCT system noise problems. OCT systems like OCT scanner 12 illustrated in FIG. 1 (discussed above) are subject to three major noise sources; receiver-amplifier noise; shot noise: and excess intensity noise. Receiver noise dominates in the regime where the light power $I_D$ (Eqn. 1) available at the detector is very low. The receiver noise dominated regime can usually be avoided by using state-of-the-art electronics and sufficient optical source power. When $I_{DC}$ greatly exceeds $I_{PIX}$, (Eqn. 1) the detector may enter the excess intensity noise regime where the effective signal-to-noise ratio (SNR) is degraded. Excess intensity noise dominates in the regime where the light power $I_D$ at the detector is very high so that more light power does not improve effective sample SNR at the detector and may instead reduce SNR if the additional light power consists only of the $I_{DC}$ term. To avoid the excess intensity noise dominated regime, the reference light intensity $I_R$ is usually attenuated, typically by a factor of 100 or more, to reduce $I_{DC}$ with respect to $I_{PIX}$. Shot noise arises from the inherent quantum nature of light and cannot be avoided, so it dominates in the intermediate regime between the receiver noise and excess intensity noise regimes. However, in the shot noise regime, sensitivity improves linearly with the light power $I_S'$ backscattered by the sample. For a given source power, the optimum OCT system sensitivity is achieved when operating in the shot noise dominated regime but this condition limits the usefulness of the available source power, most of which must be discarded to avoid the excess intensity noise regime.

Useful OCT scanning speed depends on the available OCT detector channel sensitivity. The OCT detector sensitivity problem includes the excess intensity noise issue mentioned by Podoleanu and Jackson (above) and also other issues, such as the polarization distortion problem discussed, for example, in U.S. Pat. No. 6,134,003 issued to Tearney et al., who suggest using Faraday rotators or optical circulators in a fiber optic OCT apparatus to improve OCT system sensitivity. Similar OCT system designs with improved sensitivity, based on optical circulators, have been suggested for high speed imaging applications by Rollins et al. [A. M. Rollins and J. A. Izatt, "Optimal interferometer designs for optical coherence tomography," Opt. Lett. 24 1484–6, November 1999] and in U.S. Pat. No. 6,657,727 issued to Izatt et al. Elsewhere, in U.S. Pat. No. 6,615,072, Izatt et al. also suggest using a polarizing element, such as a Faraday rotator or optical circulator, on the optical path to compensate for variations in interference intensity at the detector caused by variation in fiber birefringence in a power effective fiber optic OCT probe apparatus. Similarly, in U.S. Pat. No. 6,385,358, Everett et al. describe a birefringence insensitive OCDR system that uses a Faraday rotator to cancel polarization mismatch arising from the use of inexpensive disposable non-polarization maintaining optical fiber in the sample arm, thereby permitting its use in various disposable clinical devices such as catheters, guidewires, and hand-held instruments or probes. In U.S. Pat. No. 5,202,745, Sorin et al. discuss an OCDR system that employs polarization diversity signal processing methods to overcome the effects on OCT detection sensitivity of the polarization distortion usually found in optical fibers and other system components. Disadvantageously, for some applications, polarizing elements such as Faraday rotators and optical circulators may be too expensive with respect to simple polarizing elements and retardation plates. Further, the optical circulator is presently only available for the wavelength range of 1300–1550 nm, and not for the 800 nm region preferred for retinal OCT.

The typical Michelson interferometer splits the source beam power equally into a sample arm signal $S_S$ and a reference arm signal $S_R$ (FIG. 1). After reflection of the light from the sample, 50% of the reflected sample light is directed to the detector and 50% toward the source. Therefore, with a sample reflectivity R, only $0.5 \times 0.5 \times R = 0.25 \times R$ of the source light power reaches the detector by way of the sample. A similar fraction of 0.25 of the emitted light power reaches the detector by way of the reference arm, assuming a reference mirror reflectivity of 100%. Disadvantageously, the reference power $I_R$ (Eqn. 1) must often then be further attenuated to avoid the excess intensity noise dominated regime at the detector. For example, Hoeling et al. [B. Hoeling, A. Fernandez, R. Haskell, E. Huang, W. Myers, D. Petersen, S. Ungersma, R. Wang, M. Williams and S. Fraser, "An optical coherence microscope for 3-dimensional imaging in developmental biology," Opt. Express, 6, 136–145 (2000)] suggest reducing the reference power by 75% to improve detector SNR by 40% by avoiding the excess intensity noise regime.

There is accordingly a clearly felt need in the art for an OCT imaging technique that can inexpensively resolve these test sample motion artifact and detector sensitivity problems in a manner that reduces the acquisition time for accurate 3D OCT images of biological tissues, such as the retina. These unresolved problems and deficiencies are clearly felt in the art and are solved by this invention in the manner described below.

SUMMARY OF THE INVENTION

This invention solves the optical coherence tomography (OCT) detector sensitivity problem for the first time by disposing a polarizing beam splitter in an OCT interferometer to adjust optical source signal intensities simultaneously in the reference and sample arms so that noise-limited three-dimensional (3D) OCT channel sensitivity is optimized. This invention solves the test sample motion artifact problem for the first time by using a low-frequency OCT detector output component to generate a scanning laser ophthalmoscope-like (SLO-like) image simultaneously (pixel by pixel) with each corresponding OCT en face image for use in realigning the sequential OCT en face images to remove motion artifacts. This invention arose in part from the unexpectedly advantageous observation that the method of this invention for optimizing the detector signal-to-noise ratio (SNR) largely reduces the low-frequency detector output components generated by the reference light, which usually overlay the low-frequency detector output components generated by the sample light. This reference component reduction eliminates the usual washout of the weaker signal components, thereby making them available to provide SLO-like image data useful for reducing motion artifacts in the OCT en face image data. The enhanced OCT channel sensitivity and absence of additional optical components and channel detectors in the system of this invention improves the available 3D image scan speed and accuracy over the prior art.

The system of this invention derives a SLO-like image signal from a low-frequency component $V_L$ of the existing OCT detector output signal $V_D$, which may be obtained by means of a bandpass filter centered at a low frequency, for example. Each SLO-like image pixel is obtained simultaneously with the corresponding pixel for the corresponding OCT en face image.

Although the OCT en face image changes with sampling depth, each corresponding SLO-like image of this invention shows all features of the 3D OCT-imaged volume simultaneously, independent of sampling depth. This may be likened to a projection of the features within the 3D OCT-imaged volume on an x-y plane. Because the SLO-like image remains essentially unchanged at all sampling depths, each new SLO-like image may be quickly aligned (on the fly) with the previous SLO-like image by consulting prominent image features (e.g., vessels). The pixel remapping required for such alignment (if any) may then be recorded as a precise representation of any intervening lateral sample motion. During the recording of the OCT en face images, each shifted OCT en face image can be corrected on the fly by consulting the pixel-by-pixel remapping needed to align the corresponding SLO-like image that was simultaneously obtained using the same optical channel according to the method of this invention. Because there is a pixel-to-pixel correspondence between the simultaneous OCT and SLO-like images of this invention, the pixel motion measured for each SLO-like image can be used to correct the (xy-plane) position of the corresponding OCT en face image, thereby allowing the individual OCT en face frames to be precisely aligned on the fly to create an undistorted 3D image data set for the OCT-imaged volume.

It is a purpose of the system of this invention to provide rapid and precise 3D OCT tissue images free of motion artifacts in an OCT system without additional optical components. It is another purpose of the system of this invention to improve OCT system detector channel sensitivity and scanning speed with existing source power levels and optical components.

In one aspect, the invention is an OCT system including an interferometer having a reference arm and a sample arm each having an optical path, the sample arm being disposed such that a test sample reflects a sample portion $R_S$ of an incident optical signal $S_S$ along the sample arm optical path, a reflector disposed in the reference arm to reflect a reference portion $R_R$ of an incident optical signal $S_R$ along the reference arm optical path, a source for producing an optical source signal S having a short coherence length and a first polarization state, a polarizing beam splitter disposed to direct portions of the optical source signal S along the reference arm optical path and the sample arm optical path, a first polarizing element disposed to select (from the returning reference and sample portions $R_R+R_S$) a detector component $S_D$ having a second polarization state, and a detector disposed to produce an output signal $V_D$ representing the optical signal intensity $I_D$ of the detector component $S_D$, wherein the second polarization state is related to the first polarization state such that the detector operates in a noise-optimized regime.

In another aspect, the invention is an OCT system including an interferometer having a reference arm and a sample arm each having an optical path, the sample arm being disposed such that a test sample reflects a sample portion $R_S$ of an incident optical signal $S_S$ along the sample arm optical path, a reflector disposed in the reference arm to reflect a reference portion $R_R$ of an incident optical signal $S_R$ along the reference arm optical path, an optical source for producing an optical source signal S having a short coherence length, a beam splitter disposed in the interferometer to direct the optical source signal S along the reference arm optical path and the sample arm optical path, a detector disposed to produce an output signal $V_D$ representing the optical signal intensity $I_D$ of the optical signals returning from the reference mirror and the test sample, a filter coupled to the detector for separating (from the output signal $V_D$) a low-frequency component $V_L$ representing a SLO-like image pixel, a data store for storing a plurality of pixels $\{V_H\}$ representing a two-dimensional (2D) OCT en face image and a plurality of pixels $\{V_L\}$ representing a 2D SLO-like image; and a processor for removing motion artifacts from 2D OCT en face image data in accordance with the corresponding SLO-like image data.

In yet another aspect, the invention is a machine-implemented method for rendering a three-dimensional (3D) image of a test sample including the steps of (a) producing an optical source signal S having a short coherence length and a first polarization state, (b) directing a first portion $S_R$ of the optical source signal S along a reference arm optical path and directing a second portion $S_S$ of the optical source signal S along a sample arm optical path, (c) reflecting a reference portion $R_R$ of the first portion $S_R$ along the reference arm optical path, (d) selecting (from the returning reference and sample portions $R_R+R_S$) a detector component $S_D$ having a second polarization state, and (e) producing an output signal $V_D$ representing the optical signal intensity $I_D$ of the detector component $S_D$, wherein the second polarization state is related to the first polarization state such that the detector operates in a noise-optimized regime.

In a further aspect, the invention is a machine-implemented method for rendering a three-dimensional (3D) image of a test sample including the steps of (a) producing an optical source signal S having a short coherence length, (b) directing a first portion $S_R$ of the optical source signal S along a reference arm optical path and directing a second portion $S_S$ of the optical source signal S along a sample arm optical path, (c) reflecting a reference portion $R_R$ of the first portion $S_R$ along the reference arm optical path, (d) selecting (from the returning reference and sample portions $R_R+R_S$) a detector component $S_D$, (e) producing an output signal $V_D$ representing the optical signal intensity $I_D$ of the detector component $S_D$, (f) separating (from the output signal $V_D$) a low-frequency component $V_L$ representing a SLO-like image pixel and a high-frequency component $V_H$ representing an OCT image pixel, (g) storing at least one value $V_H$ representing a 2D OCT en face image pixel, and (h) removing a motion artifact from 2D OCT en face image data in accordance with the corresponding SLO-like image data.

Finally, in yet another aspect, the invention is a computer program product for use in an OCT system including an interferometer having a reference arm and a sample arm each having an optical path, the sample arm being disposed such that a test sample reflects a sample portion $R_S$ of an incident optical signal $S_S$ along the sample arm optical path, a reflector disposed in the reference arm to reflect a reference portion $R_R$ of an incident optical signal $S_R$ along the reference arm optical path, an optical source for producing an optical source signal S having a short coherence length, a beam splitter disposed in the interferometer to direct the optical source signal S along the reference arm optical path and the sample arm optical path, a detector disposed to produce an output signal $V_D$ representing the optical signal intensity $I_D$ of the optical signals returning from the reference mirror and the test sample and a filter coupled to the detector for separating, from the output signal $V_D$, a low-frequency component $V_L$ representing a SLO-like image pixel, the computer program product including a recording medium, means recorded on the recording medium for directing the OCT system to store at least one value $V_H$ representing a two-dimensional (2D) OCT en face image pixel and store at least one value $V_L$ representing a 2D SLO-like image pixel, and means recorded on the recording medium for directing the OCT system to remove a motion artifact from 2D OCT en face image data in accordance with the corresponding SLO-like image data.

The foregoing, together with other objects, features and advantages of this invention, can be better appreciated with reference to the following specification, claims and the accompanying drawing.

BRIEF DESCRIPTION OF THE DRAWINGS

For a more complete understanding of this invention, reference is now made to the following detailed description of the embodiments as illustrated in the accompanying drawing, in which like reference designations represent like features throughout the several views and wherein.

DESCRIPTION OF THE PREFERRED EMBODIMENT

Introduction

As described below in connection with FIGS. 3 and 4, some power-efficient embodiments of the system of this invention avoid wasting the available source power by exploiting certain polarization properties of the optical reference and sample signals.

As described below in connection with FIG. 5, some high-speed embodiments of the system of this invention use a low-frequency component $V_L$ of the optical coherence tomography (OCT) detector output signal $V_D$ to obtain the pixels $\{V_L\}_n$ in a scanning laser ophthalmoscope-like (SLO-like) image suitable for use in correcting the corresponding transverse en face image pixels $\{V_H\}_n$ to eliminate motion artifacts from the resulting three-dimensional (3D) OCT image pixels $\{\{V_H\}_n\}$.

As described below in connection with FIGS. 8 and 9, some embodiments of the method of this invention avoid wasting the available source power by exploiting certain polarization properties of the optical reference and sample signals and other embodiments use a low-frequency component $V_L$ of the OCT detector output signal $V_D$ to obtain the pixels $\{V_L\}_n$ in a SLO-like image suitable for use in correcting the corresponding transverse OCT en face image pixels $\{V_H\}_n$ to eliminate motion artifacts from the resulting 3D OCT image pixels $\{\{V_H\}_n\}$.

Power-Efficient OCT System Embodiments Using Polarization

Figure 3:
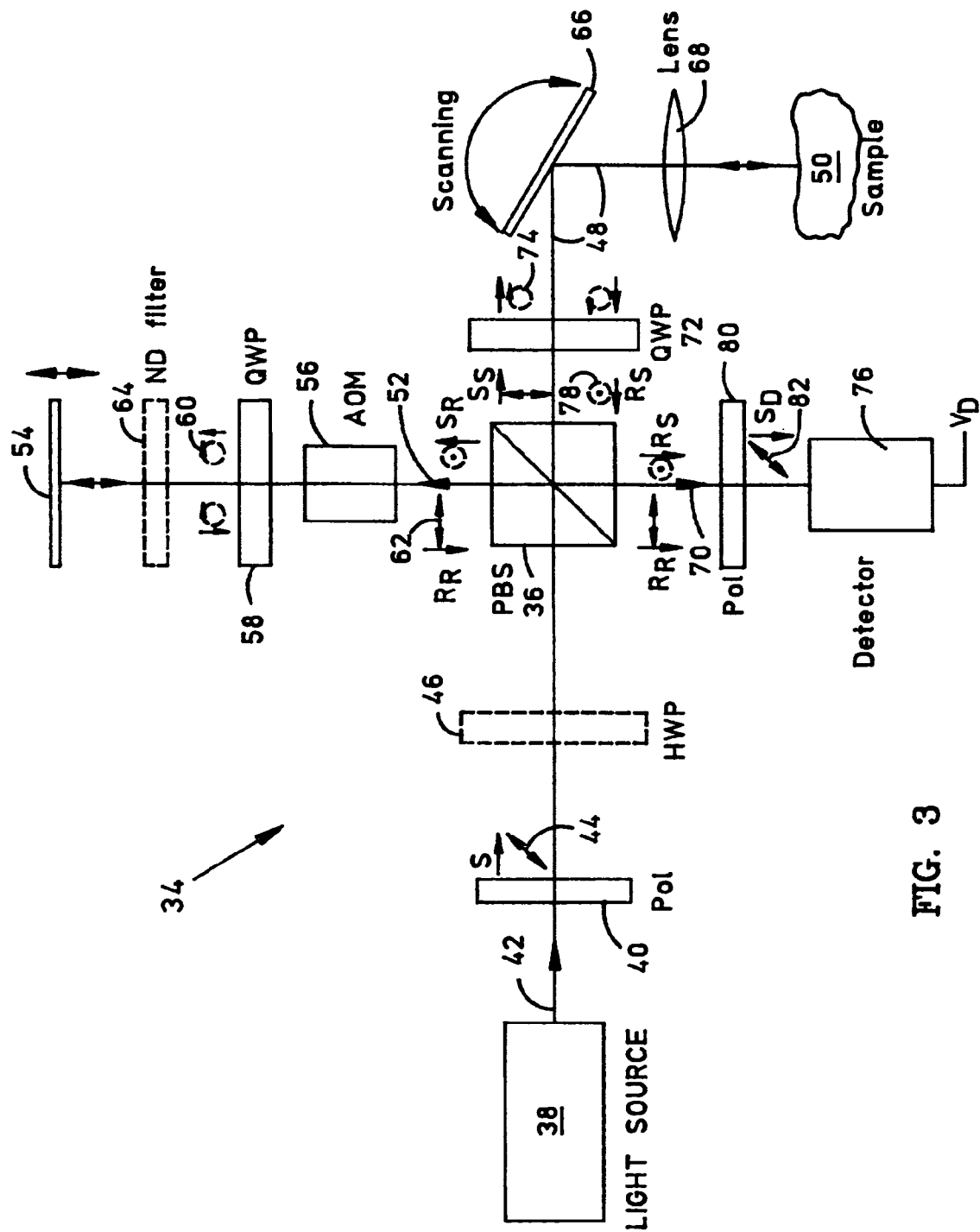
FIG. 3 is a functional block diagram illustrating a Michelson embodiment of the OCT system of this invention showing one example of the signal polarization states necessary to operate the detector in a noise-optimized regime.

FIG. 3 is a functional block diagram illustrating a Michelson embodiment 34 of the OCT system of this invention showing one example of the signal polarization states necessary to operate the detector in a noise-optimized regime. System 34 uses the polarization properties of the optical signals to avoid wasting source power. The usual non-polarizing beam splitter of the Michelson interferometer is replaced by a polarizing beam splitter (PBS) 36, which reflects optical signals having a vertically-oriented linear polarization state and transmits optical signals having a horizontally-oriented linear polarization state. The source 38 is linearly polarized by, for example, using a polarized light emitting source (not shown) or by adding a linear polarizer 40 disposed as shown. When a partly polarized light source (e.g. one of many suitable types of super luminescent diodes) is used instead of source 38, polarizer 40 should be oriented to transmit maximum power so that both source 38 and polarizer 40 may then be rotated about the optic axis 42 to obtain a source signal S of the desired polarization state 44. When a polarized light source is used instead of source 38, polarizer 40 may be omitted and only source 38 need be rotated to obtain a source signal S of desired polarization state 44. Alternatively, source 38 and polarizer 40 may remain fixed and a half-wave plate (HWP) 46 may be disposed as shown and rotated to obtain a source signal S of the desired polarization state.

Desired source signal polarization state 44 is oriented such that about, for example, 95% of the source light intensity is horizontally-oriented as a sample signal $S_S$ for direction along the sample arm optical path 48 towards the test sample 50, leaving about 5% of the source intensity vertically-oriented for direction as a reference signal $S_R$ along the reference arm optical path 52 to the reference reflector 54, which is disposed to move in either direction along the z-axis as shown by the arrows. This 19-to-1 signal splitting ratio may be varied as needed to optimize the OCT detector sensitivity by, e.g., rotating source polarizer 40, or rotating HWP 46 disposed in front of PDS 36 or any other suitable method of adjusting the desired signal polarization state 44. PBS 36 reflects the vertically-oriented reference signal $S_R$ towards reference arm optical path 52 and transmits the horizontal-oriented sample signal $S_S$ along sample arm optical path 48 towards sample 50.

Figure 2:
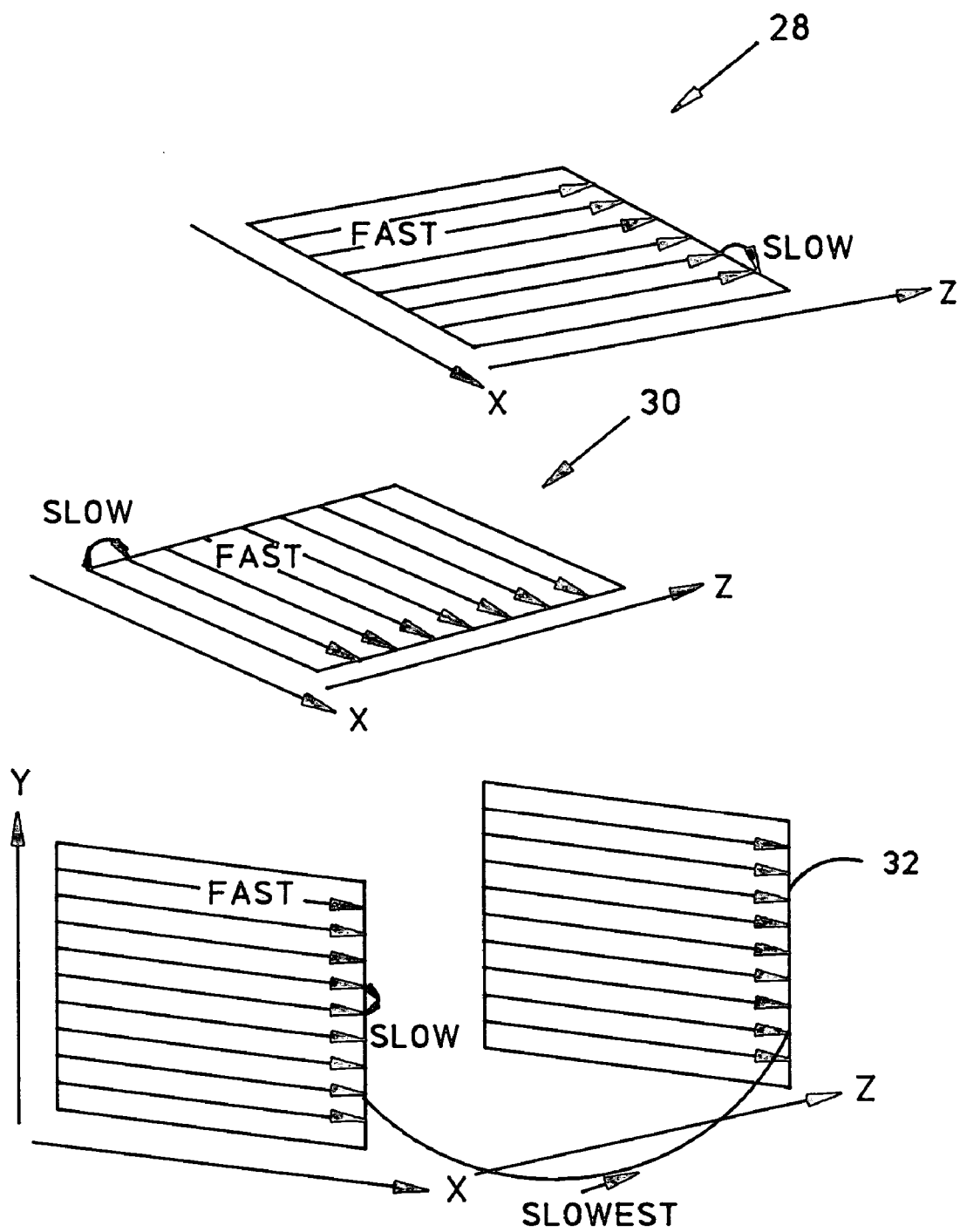
FIG. 2 is a functional diagram illustrating several three-dimensional (3D) OCT image scanning patterns from the prior art.

Reference arm optical path 52 may also include an acousto-optic modulator (AOM) 56 for shifting the frequency of reference signal $S_R$ and a quarter-wave plate (QWP) 58 disposed to change the polarization state of reference arm signal $S_R$ to a circular polarized state 60 and to recover a horizontally-oriented linear polarization state 62 after the reflected reference signal portion $R_R$ returns through QWP 58. A ND filter 64 may be disposed in the usual manner in reference arm optical path 52 to attenuate reference signal power $I_R$ but this technique wastes source power that would otherwise be available for improved SNR in the detected sample signal portion $R_S$. Sample arm optical path 48 may also include a scanning apparatus 66 for redirecting sample signal $S_S$ over a two-dimensional (2D) region of sample 50 (e.g., en face image 32 in FIG. 2) and a focusing lens 68 for establishing the sample image spot size.

After transiting ND filter 64, reference signal $S_R$ illuminates reference reflector 54 and reflected reference signal portion $R_R$ propagates back through ND filter 64 and QWP 58. Reflected reference signal portion $R_R$ now has polarization state 62 that is transmitted through PBS 36 along the detector arm optical path 70. Sample signal $S_S$ transits the QWP 72 to obtain a circularly-polarized state 74 and illuminates sample 50 by way of scanning apparatus 66 and lens 68 and perhaps other optical elements (not shown). The backscattered sample signal portion $R_S$ from sample 50 propagates back along sample arm optical path 48, returning through QWP 72 to obtain a vertically-oriented plane polarization state 78 that is reflected at PBS 36 along detector arm optical path 70 towards the photodetector 76.

QWP 58 in reference arm 52 and QWP 72 in sample arm 48 each serving to rotate the polarization plane of the respective optical signal by 90-degrees at double pass along the respective optical path. So the reflected reference signal portion $R_R$ returning to PBS 36 along reference arm optical path 52 is rotated by 90-degrees with respect to reference signal $S_R$ by two transits through QWP 58 and the reflected sample signal portion $R_S$ returning to PBS 36 along sample arm optical path 48 is also rotated by 90-degrees with respect to sample signal $S_S$ by two passes through QWP 72. Thus, nearly 100% of the reflected reference signal portion $R_R$ and the reflected sample signal portion $R_S$ is directed towards photodetector 76 by PBS 36.

Because the returning reference and sample signal portions $R_R$ and $R_S$ are now in orthogonal polarization states, they cannot interfere directly at detector 76. A second polarizer 80 is disposed as shown in front of detector 76 to extract interferable components (having the polarization state 82) from reference and sample signal portions $R_R$ and $R_S$. The ratio of the reference and sample beam powers at detector 76 may be adjusted to optimize OCT detector sensitivity by selecting an optimal polarization state 82 for the interferable components that pass through polarizer 80 by, e.g., rotating polarizer 80. A typical useful selection is that needed to transmit about 95% of the power of the reflected sample signal portion $R_S$ and about 5% of the power of the reflected reference signal portion $R_R$. The two returning signal portions of $R_R$ and $R_S$ that transmit polarizer 80 are superimposed on detector 76, which produces an electric output signal $V_D$ corresponding to an interference signal when the reflecting point from sample 50 is located at an optical distance from PBS 36 equal to the reference arm path length. This signal is further amplified, recorded, processed, and displayed.

In this example, the initial reference signal $S_R$ is attenuated by approximately 400 times between polarizer 40 and detector 76, which is an exemplary value suggested to avoid operating detector 76 in the excess intensity noise regime. Conversely, in this example, the initial sample signal $S_S$ is attenuated only by about ten percent (additional to the test sample reflectance ratio $R_O$) between polarizer 40 and detector 76 because a fraction of $0.95 \times 0.95 \times R_O$ reaches detector 76 by way of sample 50. This yields a detector sensitivity improvement of about 5.5 dB over the nearly 75% sample signal attenuation (additional to the test sample reflectance ratio $R_O$) known for the OCT configurations known in the art.

In system 34 of FIG. 3, polarizer 40 (or HWP 46 or both) and polarizer 80 may be reoriented to optimize the distribution of optical signal power among the optical paths in sample arm 48, reference arm 52 and detector arm 70 to achieving optimal OCT detector sensitivity, which is achieved when detector 76 is operated in the shot noise regime. When signal power in reference arm 52 is too high, detector 76 operates in the excess intensity noise domain. When signal power is too low in the reference arm, detector 76 operates in the receiver (thermal) noise domain. With the system of this invention, power in reference arm 52 may be attenuated to avoid the excess intensity noise domain without losing the available source power, which may be instead diverted to sample arm 48 to improve sample signal portion $R_S$ and thus optimize SNR; a careful adjustment of the polarizer settings avoids both, excess intensity and receiver noise domain.

The following table lists theoretical sensitivity improvement of the system of this invention compared to conventional OCT systems from the prior art obtained for different settings of polarizer 40 and polarizer 80. The polarizer angle settings refer to the horizontal state.

| Example | Polarizer 40 | Polarizer 80 | Sensitivity Gain |
| --- | --- | --- | --- |
| A | 45.0° | 45.0° | 0.0 dB |
| B | 12.9° | 45.0° | +2.8 dB |
| C | 12.9° | 77.1° | +5.5 dB |

Example A does not improve OCT detector sensitivity because it is equivalent to the conventional OCT operation that omits polarizers 40 and 80, HWP 46 and QWPs 58 and 72, replaces PBS 36 with a nonpolarizing beam splitter, and includes ND filter 64 with a double-pass attenuation factor of 100. In Example C, ND filter 64 is omitted and the entire requisite attenuation of reference signal power is achieved by the polarizer settings alone, with nearly all of the available light power diverted to reach detector 76 by way of sample arm optical path 48.

Figure 4:
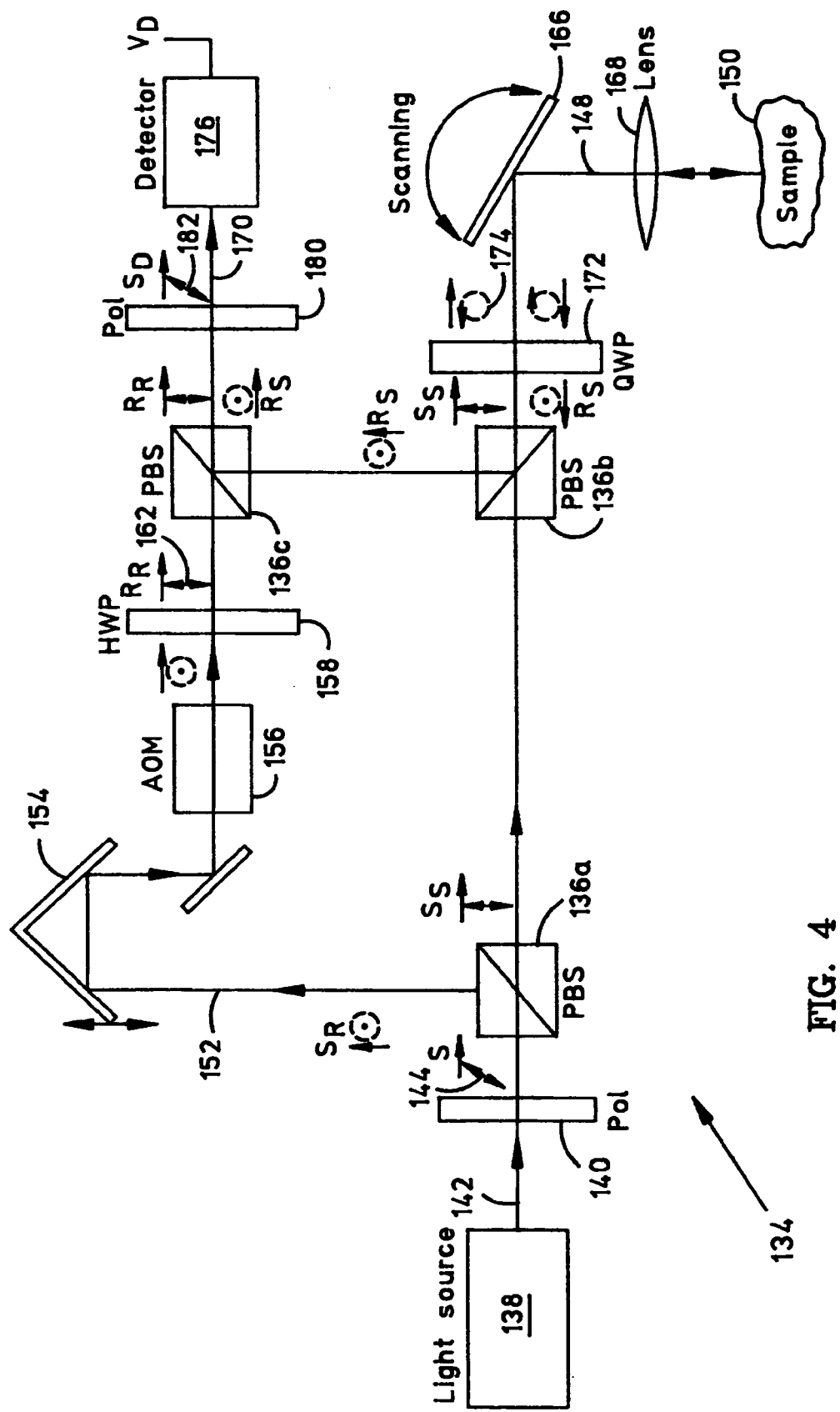
FIG. 4 is a functional block diagram illustrating a Mach-Zehnder embodiment of the OCT system of FIG. 3.

FIG. 4 is a functional block diagram illustrating a Mach-Zehnder embodiment 134 of the OCT system of FIG. 3 that may be appreciated with reference to the above description of FIG. 3, wherein the descriptive numerals for items having like functions to those disclosed in FIG. 3 are incremented by 100 so that, for example, the operation of the three PBSs 136a, 136b and 136c together may be fully appreciated with reference to the above description of PBS 36 shown in FIG. 3. The working principle of system 134 is essentially similar to that of system 34 discussed above. The function of QWP 58 in system 34 (through which pass both reference signals $S_R$ and $R_R$) is assumed in system 134 by the HWP 158, through which passes only the reflected reference signal portion $R_R$ alone. The z-axis positioning function of reference reflector 54 is assumed by the path delay reflector 154, which is disposed to move in either direction along the z-axis as shown by the arrows. The functions of HWP 46 and ND filter 64, being optional in the system of this invention, are omitted from FIG. 4 for simplicity.

OCT System Embodiments Using SLO-Like Images

Figure 5:
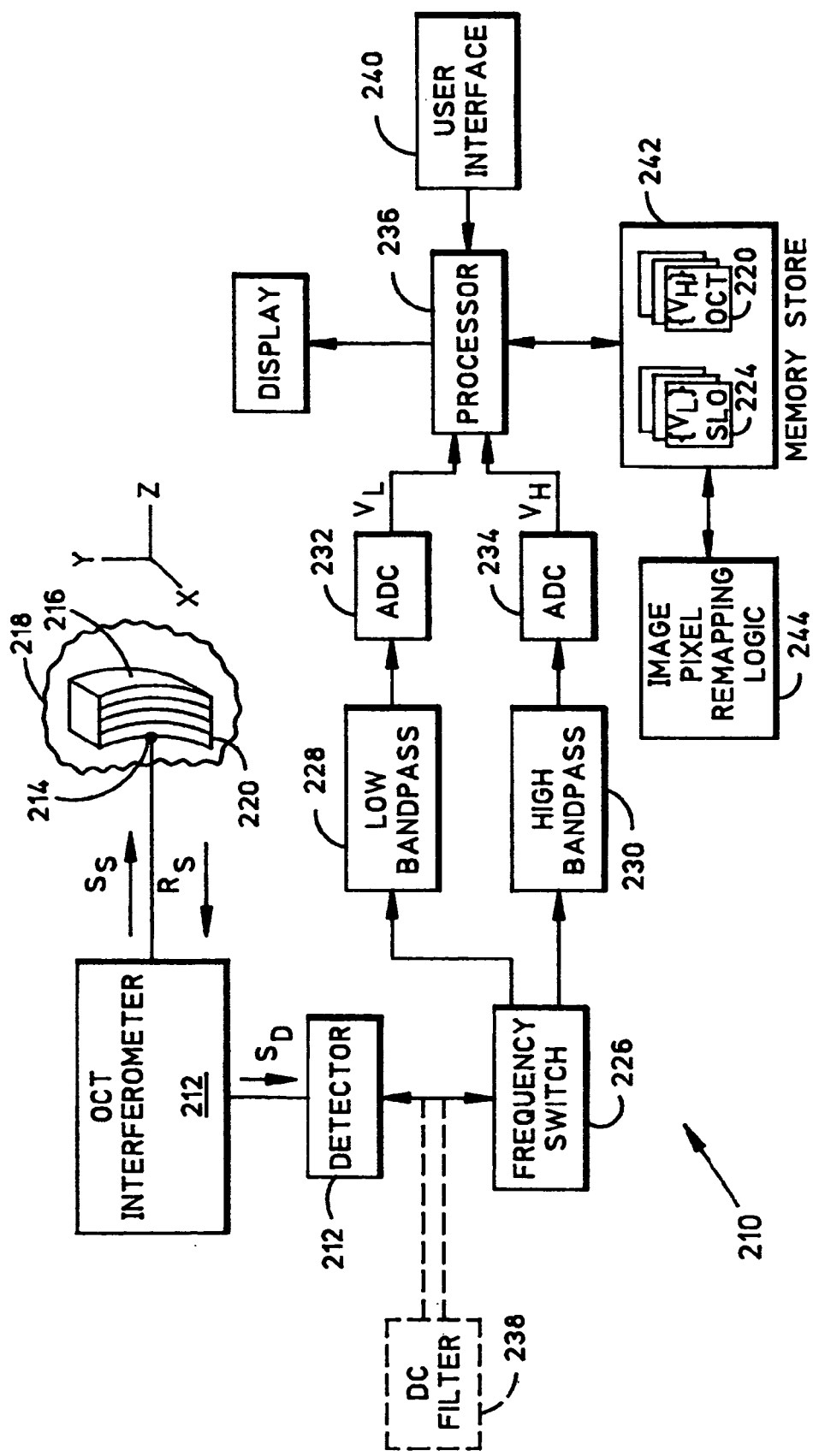
FIG. 5 is a functional block diagram illustrating an exemplary embodiment of the OCT system of this invention having an exemplary OCT and scanning laser ophthalmoscope-like (SLO-like) image processing arrangement suitable for removing motion artifacts from a three-dimensional (3D) OCT image.

FIG. 5 shows an OCT system 210 having an exemplary OCT and SLO-like image processing arrangement suitable for removing motion artifacts from a 3D OCT image.

Figure 1:
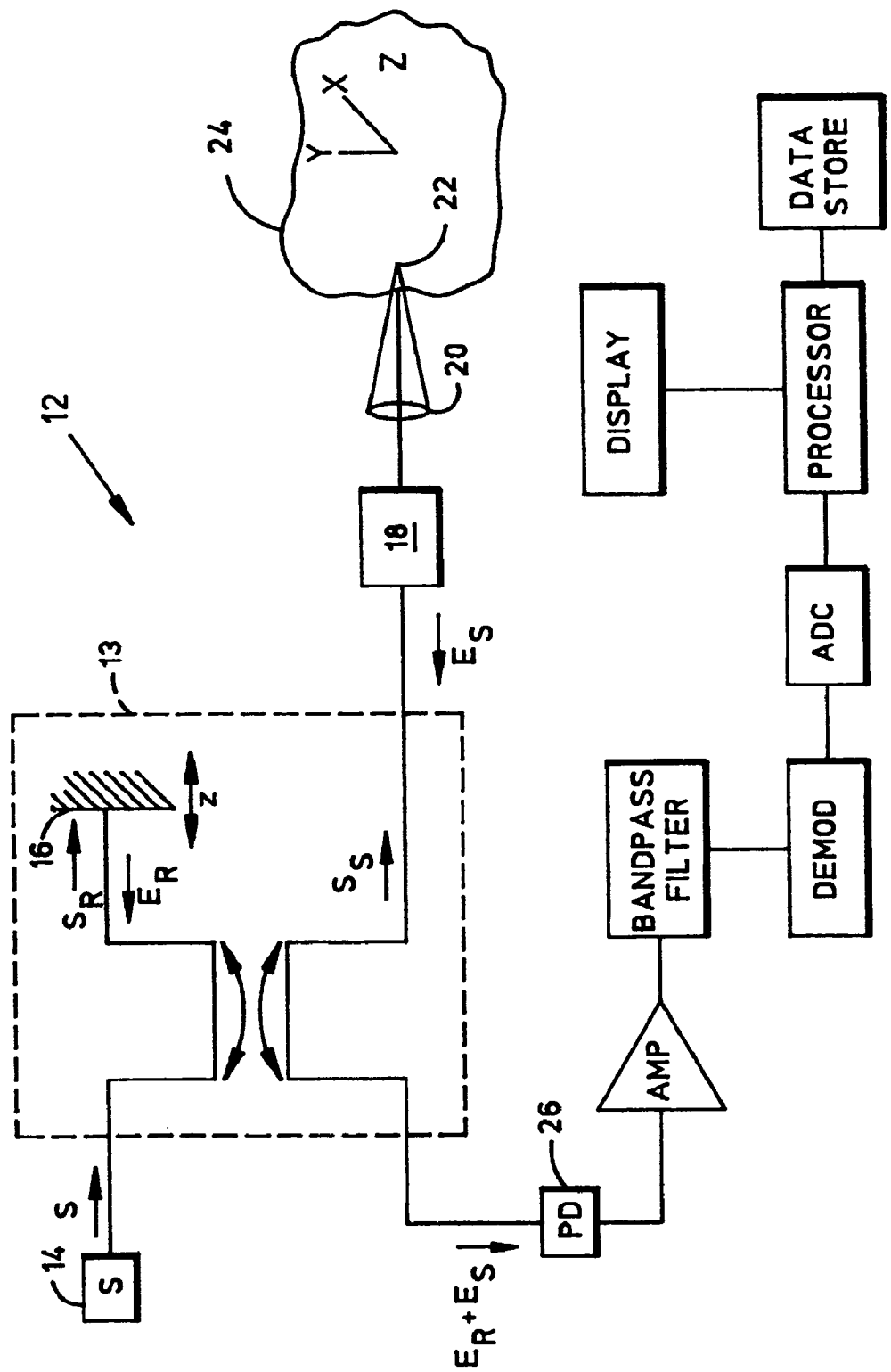
FIG. 1 is a functional block diagram illustrating the typical optical coherence tomography (OCT) system from the prior art, including a Michelson interferometer.
Figure 7:
FIG. 7 illustrates a typical two-dimensional (2D) SLO-like image of the retina in accordance with this invention.
Figure 6:
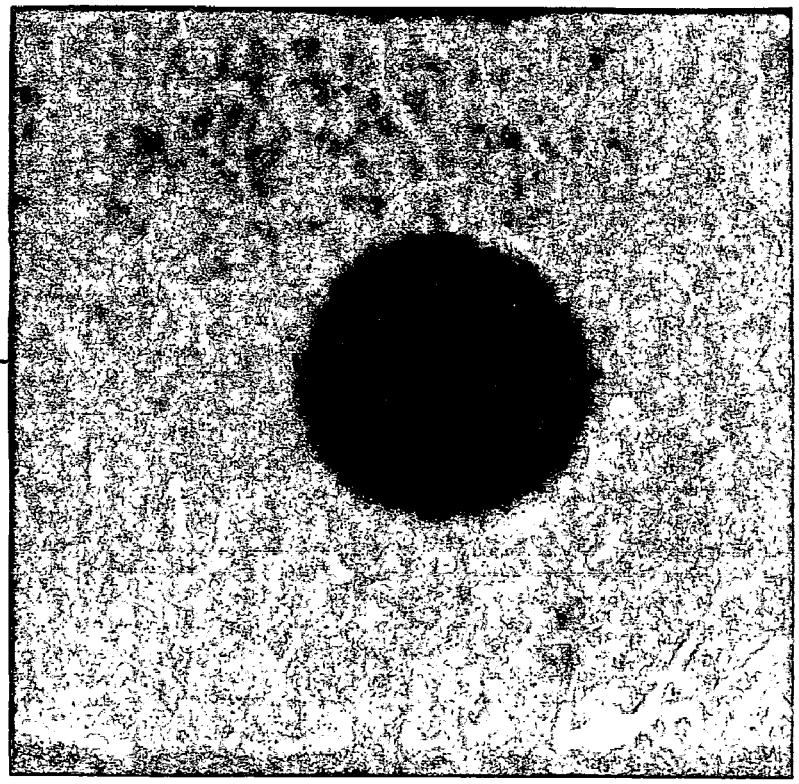
FIG. 6 illustrates a typical two-dimensional (2D) OCT en face image of the retina in accordance with this invention.

System 210 includes an interferometer assembly 212 that may be understood with reference to the above discussion in connection with, for example, FIGS. 1 and 3–4. Interferometer assembly 212 directs an optical sample signal $S_S$ at one point 214 within the 3D OCT volume 216 of the test sample 218. OCT volume 216 includes a plurality of two-dimensional (2D) en face images exemplified by the 2D en face image slice 220, which is also illustrated in FIG. 6. Optical sample signal $S_S$ is backscattered from point 214 as the returning optical sample portion $R_S$. Interferometer assembly 212 directs an optical detector component $S_D$ to the detector 222, which produces an OCT detector output signal $V_D$ that includes DC, low-frequency and high-frequency components. System 210 uses a low-frequency component $V_L$ of OCT detector output signal $V_D$ to obtain the pixels $\{V_L\}_n$ in a SLO-like image such as the image 224 illustrated in FIG. 7. As discussed in the above-cited Hitzenberger patent, OCT detector output signal $V_D$ typically includes a high-frequency component $V_H$ (above 10 MHz) generated by interference of the returning optical reference and sample signal portions ($R_R$ and $R_S$) whose optical frequencies are shifted with respect to each other by some useful means, e.g., AOM 56 in FIG. 3. High-frequency component $V_H$ is used in OCT system 210 to obtain each of the pixels $\{V_H\}_n$ (n=1, N) in 2D en face image slice 220 and in each of a plurality N of such OCT en face image slices in 3D OCT volume 216.

However, low-frequency output signal component $V_L$ includes the total intensity of returning sample signal portion $R_S$ (integrated over the entire depth of the sample) before demodulation. The problem with exploiting sample signal component $V_L$ at this stage is that it is usually overlaid by the relatively large DC intensity component of returning reference signal portion $R_R$, which may exceed the desired signal by one or more orders of magnitude. Without more, the DC intensity of reference signal portion $R_R$ may force OCT detector 222 into the excess intensity noise regime, washing out the low-frequency component of sample signal portion $R_S$ and thereby prevent the recovery of useful SLO-like images of test sample 218. This problem may be overcome in interferometer 212 by attenuating the optical reference signal intensity $I_R$ by a factor of one hundred or more, thereby improving the SNR of SLO-like image pixels $\{V_L\}$, although this technique wastes source power that would otherwise be available for improved SNR in the detection of returning sample signal portion $R_S$. Preferably, the excess intensity noise regime of OCT detector 222 is avoided by exploiting certain polarization properties of the optical reference and sample signals as discussed above in connection with FIGS. 3–4.

Returning to FIG. 5, detector output signal $V_D$ is passed to a frequency switch 226 for demodulation and redistribution to a low-frequency filter 228 and a high-frequency filter 230. Low-frequency filter 228 provides low-frequency component $V_L$, which is passed to the analog-to-digital converter (ADC) 232. High-frequency filter 230 provides high-frequency component $V_H$, which is passed to the ADC 234. Digital representation of low-frequency and high-frequency components $V_L$ and $V_H$ are then passed to the processor 236 for distribution according to the method of this invention.

In some embodiments, the system of this invention includes an additional electronic band pass filter, exemplified by the DC filer 238 in system 210, to cut off the residual DC intensity of reference signal portion $R_R$ by segregating the DC term $V_{DC}$ of detector output signal $V_D$ from the intermediate-frequency component $V_L$ and the higher-frequency component $V_H$ to reduce the excess signal noise in the SLO-like image pixels $\{V^L\}$. Thereby, the DC term $V_{DC}$ and other very low frequency noise is eliminated from the SLO-like image pixels $\{V_L\}$. This filter preferably transmits output signal $V_D$ frequencies up to the imaging bandwidth. Without the lowest frequency components, the resulting SLO-like image pixels $\{V_L\}$ appear like a dark field image, showing only areas of high image contrast; i.e., abrupt intensity changes in backscattered sample signal $R_S$. While rejecting uniformly bright or dark areas, high contrast features like retinal blood vessels, etc., should be accentuated sufficiently for the purposes of the method of this invention for adjusting image pixel alignment to remove motion artifacts.

Processor 236 accepts instructions from a user interface 240 and supervises the storage and retrieval of image data from the memory store 242, wherein pixels $\{V_L\}_n$ representing the $n^{th}$ SLO-like image 224 and pixels $\{V_H\}_n$ representing the $n^{th}$ OCT en face image 220, for all values of n=1, N. The $(n+1)^{st}$ OCT en face image may change so much with respect to the $n^{th}$ one that the two cannot be easily or confidently aligned from available image features. But the $(n+1)^{st}$ SLO-like image is essentially unchanged from the $n^{th}$ SLO-like image so that each SLO-like image may be aligned on the fly with the immediately-previous SLO-like image by consulting prominent image features (e.g., vessels) using any of many useful image feature recognition procedures known in the digital image art. The necessary pixel remapping is a simple dual coordinate (a pixel shift in the x-axis and another pixel shift in the y-axis) that gives a precise representation of any lateral motion of test sample 218 intervening the two SLO-like images. Such SLO-like image (x, y) pixel shifts may be accumulated from n=1,N to realign all images to the position of the very first image in the sequence. This same test sample motion is known to intervene the same two OCT en face images so that each OCT en face image may be realigned to either the immediately-previous OCT image applying the immediate (x, y) pixel shift or the first (n=1) OCT image by applying the accumulated SLO-like image (x, y) pixel shifts to eliminate motion artifacts from the resulting 3D OCT image pixels $\{\{V_H\}_n\}$. This procedure is simple and may be implemented with digital logic such as the image pixel remapping logic 244 illustrated in FIG. 5 or by processor 236 or any other useful means. The display 245 is used to view renderings of any of the images discussed herein, including without limit the OCT en face images, slices in any dimension through the 3D OCT scan, SLO-like images and the rendered results of any available combination of the pixels representing such images.

Other Embodiments

Figure 8:
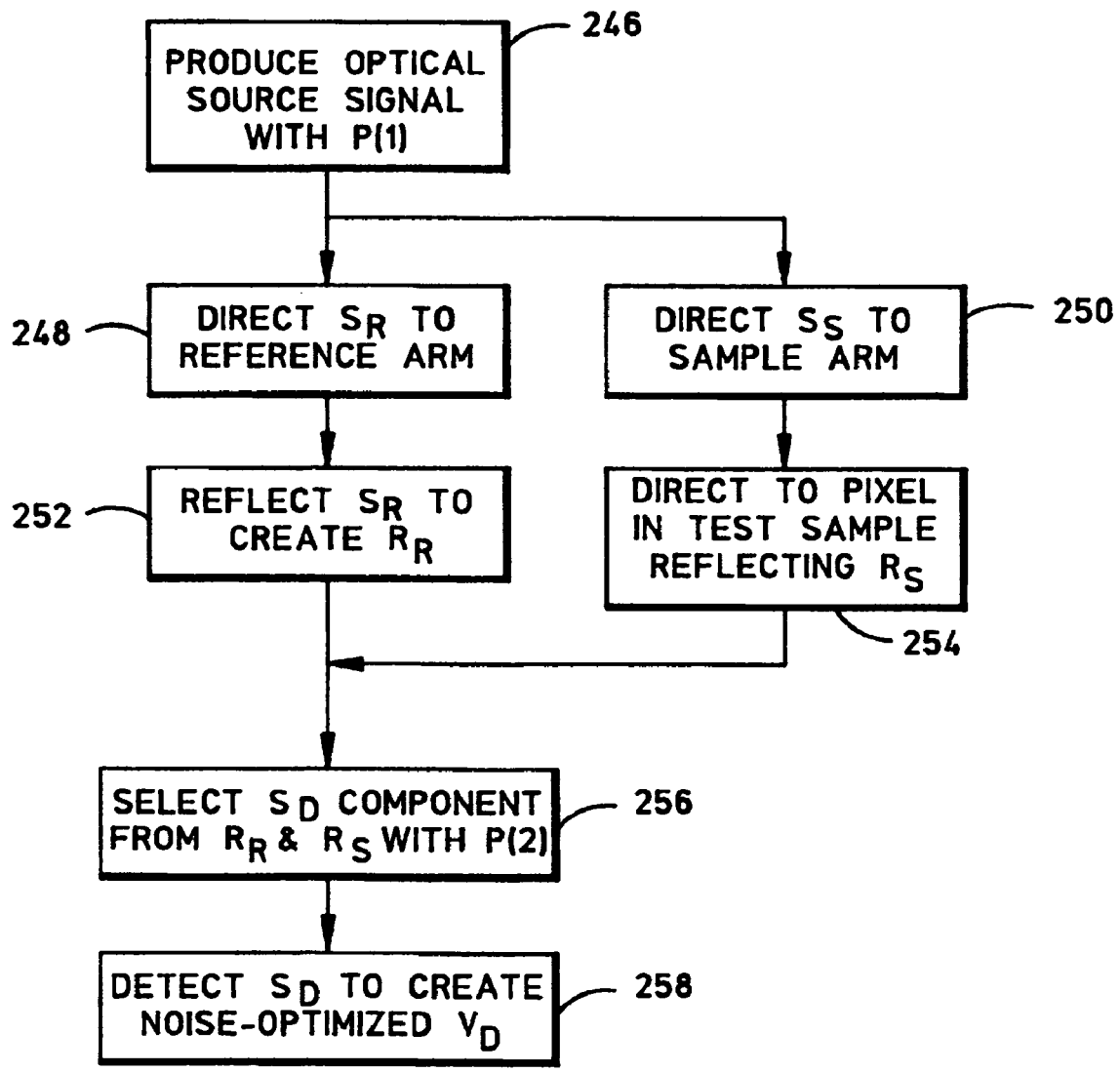
FIG. 8 is a flow chart diagram illustrating one embodiment of the method of this invention for producing a 3D OCT scan of a test sample.

FIG. 8 illustrates one embodiment of the method of this invention for producing a 3D OCT scan of a test sample. In the first step 246, a short-coherence optical signal S is produced having a first polarization state P(1). A portion $S_R$ of optical signal S directed to a reference arm of an interferometer in the step 248 and another portion $S_S$ of optical signal S directed to a sample arm of the same interferometer in the step 250. In the step 252, the portion $S_R$ is reflected to create the reflected reference signal portion $R_R$. In the step 254, the portion $S_S$ is directed to the pixel under test in the test sample, which reflects an optical sample signal portion $R_S$. A component $S_D$ having a second polarization state P(2) is selected from the combination of the returning optical signal portions $R_R$ and $R_S$ in the step 256 and presented to a detector, which produces a representative output signal $V_D$ in the final step 258. The second polarization state P(2) is related to the first polarization state P(1) such that the detector is noise-optimized.

Figure 9:
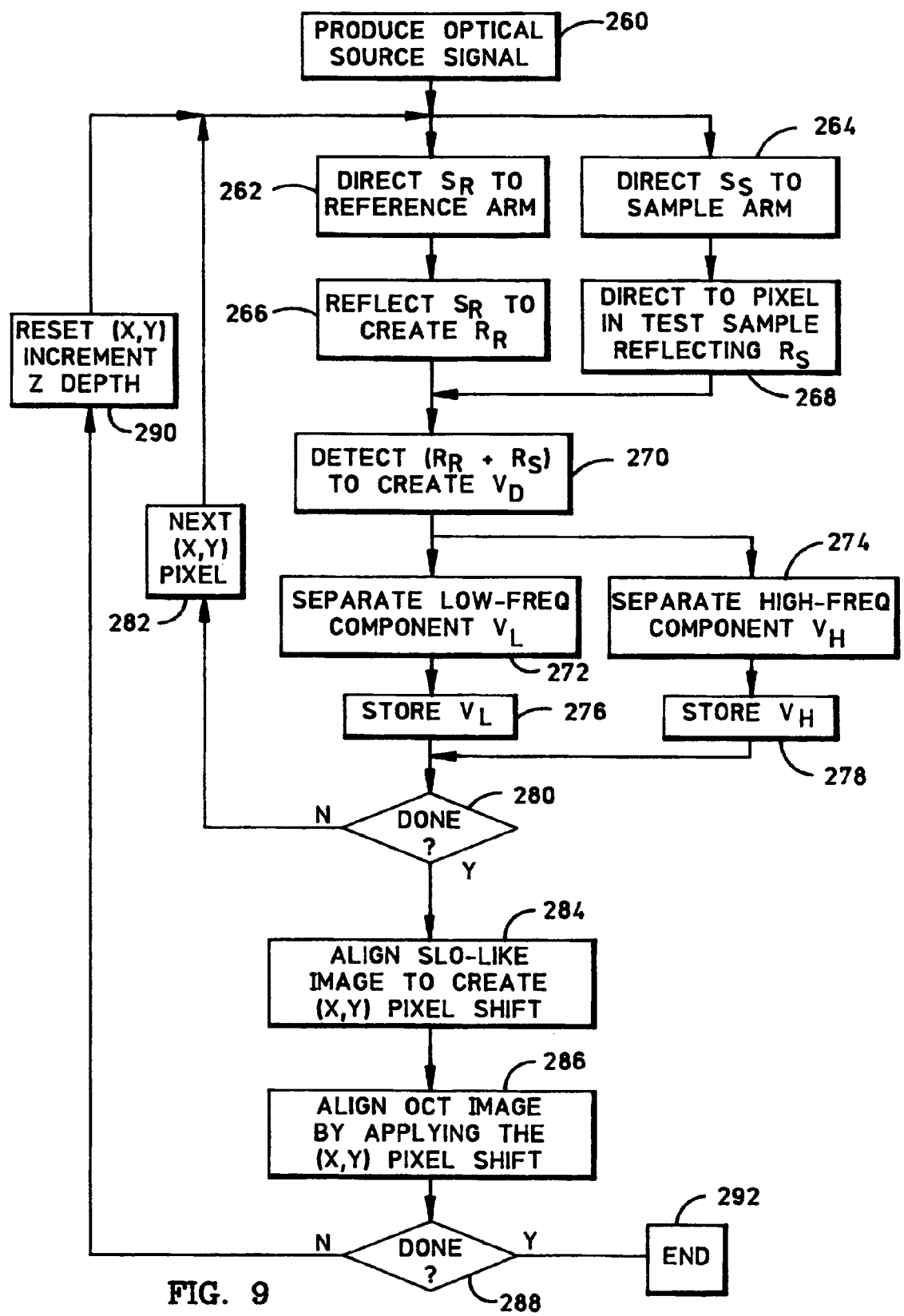
FIG. 9 is a flow chart diagram illustrating an alternate embodiment of the method of this invention for producing a 3D OCT scan of a test sample.

FIG. 9 illustrates an alternate embodiment of the method of this invention for producing a 3D OCT scan of a test sample. In the first step 260, a short-coherence optical signal S is produced. A portion $S_R$ of optical signal S directed to a reference arm of an interferometer in the step 262 and another portion $S_S$ of optical signal S directed to a sample arm of the same interferometer in the step 264. In the step 266, the portion $S_R$ is reflected to create the reflected reference signal portion $R_R$. In the step 268, the portion $S_S$ is directed to the pixel under test in the test sample, which reflects an optical sample signal portion $R_S$. The returning optical signal portions $R_R$ and $R_S$ are presented to a detector, which produces a representative output signal $V_D$ in the step 270. In the next steps 272 and 274, the low-frequency and high-frequency components, $V_L$ and $V_H$ respectively, are separated from output signal $V_D$ and stored in the next steps 276 and 278, respectively. At the step 280, the procedure asks whether the current 2D image scan is completed; if not, then the step 282 increments the x-axis and/or y-axis pixels and returns to step 262. Otherwise, the next step 284 compares the $n^{th}$ just-completed SLO-like image represented by the pixels $\{V_L\}_n$ with the $(n-1)^{st}$ SLO-like image $\{V_L\}_{n-1}$, to recover the (x, y) pixel shift that must be applied to the later image to remove any intervening transverse motion of the test sample. In the next step 286, this (x, y) pixel shift is applied to the $n^{th}$ just-completed OCT en face image represented by the pixels $\{V_H\}_n$ to remove therefrom any intervening transverse motion of the test sample. Finally, the step 288 asks whether the 3D OCT depth scan has been completed; if not, then the step 290 resets the x-axis and y-axis pixels and increments the z-axis pixel location in the test sample and returns to step 262; if so, the procedure ends at the step 292.

Figure 10:
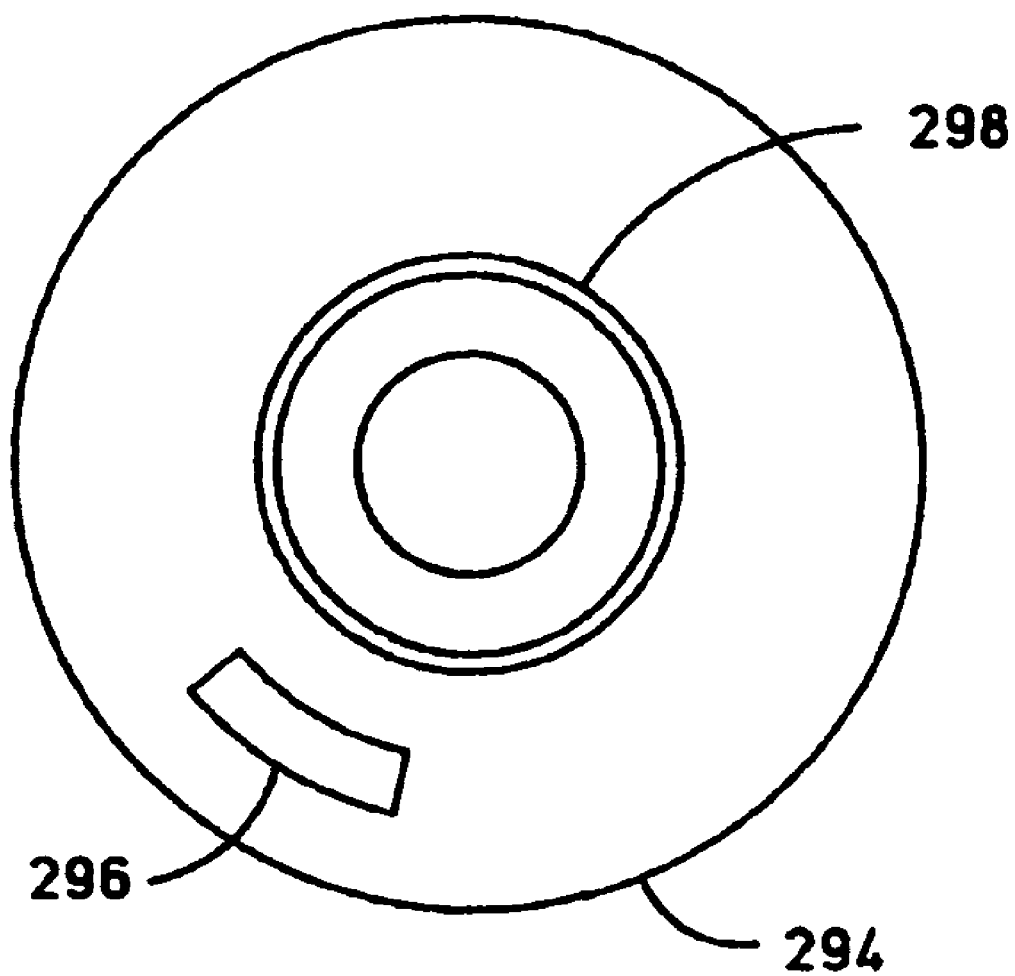
FIG. 10 illustrates an embodiment of the computer program product (CPP) of this invention.

FIG. 10 illustrates the computer program product (CPP) of this invention that includes a recording medium 294 on which is recorded software program instructions for directing an OCT system to perform the steps of the method of this invention, examples of which are discussed above in connection with FIGS. 8–9. The data storage regions 296 and 298 in recording medium 294 may illustrate such recorded software program instructions, for example.

Clearly, other embodiments and modifications of this invention may occur readily to those of ordinary skill in the art in view of these teachings. Therefore, this invention is to be limited only by the following claims, which include all such embodiments and modifications when viewed in conjunction with the above specification and accompanying drawing.

I claim:

1. An optical coherence tomography (OCT) system comprising:

an interferometer having a reference arm and a sample arm each having an optical path, the sample arm being disposed such that a test sample reflects a sample portion $R_S$ of an incident optical signal $S_S$ along the sample arm optical path;

a reflector disposed in the reference arm to reflect a reference portion $R_R$ of an incident optical signal $S_R$ along the reference arm optical path;

a source for producing an optical source signal S having a short coherence length and a first polarization state;

a polarizing beam splitter disposed to direct portions of the optical source signal S along the reference arm optical path and the sample arm optical path;

a first polarizing element disposed to select, from the returning reference and sample portions ($R_R+R_S$), a detector component $S_D$ having a second polarization state, wherein the orientation of the first polarizing element with respect to the orientation of the beam splitter is selected to transmit about ninety-five percent of the returning sample portion $R_S$ and about five percent of the returning reference portion $R_S$; and a detector disposed to produce an output signal $V_D$ representing the optical signal intensity $I_D$ of the detector component $S_D$, wherein the second polarization state is related to the first polarization state such that the detector operates in a noise-optimized regime.

2. The OCT system of claim 1 further comprising:

a scanner disposed to sweep the incident optical signal $S_S$ over at least part of the test sample; and a reflector motor disposed to move the reflector along the reference arm optical path.

3. The OCT system of claim 1 wherein the interferometer is a Michelson interferometer.

4. The OCT system of claim 1 wherein the interferometer is a Mach-Zehnder interferometer.

5. The OCT system of claim 1 further comprising:

a second polarizing element disposed in the sample arm optical path such that the returning sample portion $R_S$ is directed by the polarizing beam splitter to the detector.

6. The OCT system of claim 1 further comprising:

a second polarizing element disposed in the reference arm optical path such that the returning reference portion $R_R$ is directed by the polarizing beam splitter to the detector.

7. The OCT system of claim 1 further comprising:

in the detector, a plurality of optical transducers each disposed to produce an electrical signal responsive to the detector component $S_D$.

8. The OCT system of claim 1 wherein the second polarization state is related to the first polarization state such that the detector operates in a shot-noise limited regime.

9. An optical coherence tomography (OCT) system comprising:

an interferometer having a reference arm and a sample arm each having an optical path, the sample arm being disposed such that a test sample reflects a sample portion $R_S$ of an incident optical signal $S_S$ along the sample arm optical path;

a reflector disposed in the reference arm to reflect a reference portion $R_R$ of an incident optical signal $S_R$ along the reference arm optical path;

a source for producing an optical source signal S having a short coherence length and a first polarization state;

a polarizing beam splitter disposed to direct portions of the optical source signal S along the reference arm optical path and the sample arm optical path;

a first polarizing element disposed to select, from the returning reference and sample portions ($R_R+R_S$), a detector component $S_D$ having a second polarization state;

a detector disposed to produce an output signal $V_D$ representing the optical signal intensity $I_D$ of the detector component $S_D$;

a first filter coupled to the detector for separating, from the output signal $V_D$, a low-frequency component $V_L$ representing a scanning laser ophthalmoscope-like (SLO-like) image pixel;

first data storage means for storing a plurality of pixels $\{V_H\}$ representing a two-dimensional (2D) OCT en face image;

second data storage means for storing a plurality of pixels $\{V_L\}$ representing a 2D SLO-like image; and processing means for removing motion artifacts from 2D OCT en face image data in accordance with the corresponding SLO-like image data.

10. The OCT system of claim 9 further comprising:

a scanner disposed to sweep the incident optical signal $S_S$ over at least part of the test sample; and a reflector motor disposed to move the reflector along the reference arm optical path.

11. The OCT system of claim 9 wherein the interferometer is a Michelson interferometer.

12. The OCT system of claim 9 further comprising:

a second polarizing element disposed in the sample arm optical path such that the returning sample portion $R_S$ is directed by the polarizing beam splitter to the detector.

13. The OCT system of claim 9 further comprising:

in the processing means, rendering means for realigning the pixel data representing a 2D OCT en face image with respect to the pixel data representing another 2D OCT en face image.

14. The OCT system of claim 9 further comprising:

an attenuating element disposed in the reference arm optical path to attenuate optical signals therein.

15. The OCT system of claim 9 further comprising:

a second filter coupled to the detector for separating, from the output signal $V_D$, a high-frequency component $V_H$ representing an OCT image pixel.

16. An optical coherence tomography (OCT) system comprising:

an interferometer having a reference arm and a sample arm each having an optical path, the sample arm being disposed such that a test sample reflects a sample portion $R_S$ of an incident optical signal $S_S$ along the sample arm optical path;

a reflector disposed in the reference arm to reflect a reference portion $R_R$ of an incident optical signal $S_R$ along the reference arm optical path;

an optical source for producing an optical source signal S having a short coherence length;

a beam splitter disposed in the interferometer to direct portions of the optical source signal S along the reference arm optical path and the sample arm optical path;

a detector disposed to produce an output signal $V_D$ representing the optical signal intensity $I_D$ of the returning reference and sample portions ($R_R+R_S$);

a first filter coupled to the detector for separating, from the output signal $V_D$, a low-frequency component $V_L$ representing a scanning laser ophthalmoscope-like (SLO-like) image pixel;

first data storage means for storing a plurality of pixels $\{V_h\}$ representing a two-dimensional (2D) OCT en face image;

second data storage means for storing a plurality of pixels $\{V_L\}$ representing a 2D SLO-like image; and processing means for removing motion artifacts from 2D OCT en face image data in accordance with the corresponding SLO-like image data.

17. The OCT system of claim 16 further comprising:

a scanner disposed to sweep the incident optical signal $S_S$ over at least part of the test sample; and a reflector motor disposed to move the reflector along the reference arm optical path.

18. The OCT system of claim 16 further comprising:

an attenuating element disposed in the reference arm optical path to attenuate optical signals therein.

19. The OCT system of claim 16 further comprising:

a second filter coupled to the detector for separating, from the output signal $V_D$ a high-frequency component $V_H$ representing an OCT image pixel.

20. The OCT system of claim 16 further comprising:

in the processing means, rendering means for realigning the pixel data representing a 2D OCT en face image with respect to the pixel data representing another 2D OCT en face image.

21. In an optical coherence tomography (OCT) system including a detector having a plurality of noise-limited operating regimes and an interferometer having a reference arm and a sample arm each having an optical path, the sample arm being disposed such that a test sample reflects a sample portion $R_S$ of an incident optical signal $S_S$ along the sample arm optical path, a machine-implemented method for rendering a three-dimensional (3D) image of a test sample comprising the steps of:

(a) producing an optical source signal S having a short coherence length and a first polarization state;

(b) directing a first portion $S_R$ of the optical source signal S along a reference arm optical path and directing a second portion $S_S$ of the optical source signal S along a sample arm optical path;

(c) reflecting a reference portion $R_R$ of the first portion $S_R$ along the reference arm optical path;

(d) selecting, from the returning reference and sample portions ($R_R+R_S$), a detector component $S_D$ having a second polarization state, wherein the detector component $S_D$ comprises about ninety-five percent of the returning sample portion $R_S$ and about five percent of the returning reference portion $R_R$; and (e) producing an output signal $V_D$ representing the optical signal intensity $I_D$ of the detector component $S_D$, wherein the second polarization state is related to the first polarization state such that the detector operates in a noise-optimized regime.

22. The method of claim 21 further comprising the steps of:

(b.1) sweeping the second portion $S_S$ over at least part of the test sample; and (c.1) moving the reflector along the reference arm optical path.

23. In an optical coherence tomography (OCT) system including a detector and an interferometer having a reference arm and a sample arm each having an optical path, the sample arm being disposed such that a test sample reflects a sample portion $R_S$ of an incident optical signal $S_S$ along the sample arm optical path, a machine-implemented method for rendering a three-dimensional (3D) image of a test sample comprising steps of:

(a) producing an optical source signal S having a short coherence length and a first polarization state;

(b) directing a first portion $S_R$ of the optical source signal S along a reference arm optical path and directing a second portion $S_S$ of the optical source signal S along a sample arm optical path;

(c) reflecting a reference portion $R_R$ of the first portion $S_R$ along the reference arm optical path;

(d) selecting, from the returning reference and sample portions ($R_R+R_S$), a detector component $S_D$ having a second polarization state;

(e) producing an output signal $V_D$ representing the optical signal intensity $I_D$ of the detector component $S_D$, (f) separating, from the output signal $V_D$, a low-frequency component $V_L$ representing a scanning laser ophthalmoscope-like (SLO-like) image pixel and a high-frequency component $V_H$ representing an OCT image pixel;

(g) storing at least one value $V_H$ representing a two-dimensional (2D) OCT en face image pixel; and (h) removing a motion artifact from 2D OCT en face image data in accordance with the corresponding SLO-like image data.

24. The method of claim 23 further comprising the step of:

(g.1) storing at least one detector output component $V_L$ representing a 2D SLO-like image pixel.

25. The method of claim 23 further comprising the step of:

(hall) realigning the pixel data representing a 2D OCT en face image with respect to the pixel data representing another 2D OCT en face image.

26. In an optical coherence tomography (OCT) system including a detector having a plurality of noise-limited operating regimes and an interferometer having a reference arm and a sample arm each having an optical path, the sample arm being disposed such that a test sample reflects a sample portion $R_S$ of an incident optical signal $S_S$ along the sample arm optical path, a machine-implemented method for rendering a three-dimensional (3D) image of a test sample comprising the steps of:

(a) producing an optical source signal S having a short coherence length;

(b) directing a first portion $S_R$ of the optical source signal S along a reference arm optical path and directing a second portion $S_S$ of the optical source signal S along a sample arm optical path;

(c) reflecting a reference portion $R_R$ of the first portion $S_R$ along the reference arm optical path;

(d) selecting, from the returning reference and sample portions ($R_{R+RS}$), a detector component $S_D$;

(e) producing an output signal $V_D$ representing the optical, signal intensity $I_D$ of the detector component $S_D$;

(f) separating, from the output signal $V_D$, a low-frequency component $V_L$ representing a scanning laser ophthalmoscope-like (SLO-like) image pixel and a high-frequency component $V_H$ representing an OCT image pixel;

(g) storing at least one value $V_H$ representing a two-dimensional (2D) OCT en face image pixel; and (h) removing a motion artifact from 2D OCT enlace image data in accordance with the corresponding SLO-like image data.

27. The method of claim 26 further comprising the step of:

(g.1) storing at least one detector output component $V_L$ representing a 2D SLO-like pixel.

28. The method of claim 26 further comprising the step of:

(h.1) realigning the pixel data representing a 2D OCT en face image with respect to the pixel data representing another 2D OCT en face image.

29. The method of claim 26 further comprising the steps of:

(b.1) sweeping the second portion $S_S$ over at least part of the test sample; and (c.1)

moving the reflector along the reference arm optical path.

30. A computer program product for use in an optical coherence tomography (OCT) system including an interferometer having a reference arm and a sample arm each having an optical path, the sample arm being disposed such that a test sample reflects a sample portion $R_S$ of an incident optical signal $S_S$ along the sample arm optical path, a reflector disposed in the reference arm to reflect a reference portion $R_R$ of an incident optical signal $S_R$ along the reference arm optical path, an optical source for producing an optical source signal S having a short coherence length, a beam splitter disposed in the interferometer to direct the optical source signal S along the reference arm optical path and the sample arm optical path, a detector disposed to produce an output signal $V_D$ representing the optical signal intensity $I_D$ of the optical signals returning from the reference mirror and the test sample and a filter coupled to the detector for separating, from the output signal $V_D$, a low-frequency component $V_L$ representing a scanning laser ophthalmoscope-like (SLO-like) image pixel, the computer program product comprising:

a recording medium;

means recorded on the recording medium for directing the OCT system to store at least one value $V_H$ representing a two-dimensional (2D) OCT en face image pixel and store at least one value $V_L$ representing a 2D SLO-like image pixel; and means recorded on the recording medium for directing the OCT system to remove a motion artifact from 2D OCT en face image data in accordance with the corresponding SLO-like image data.

* * * * *